United States Patent
LaBorde, Jr. et al.

(10) Patent No.: US 10,839,946 B2
(45) Date of Patent: Nov. 17, 2020

(54) SYSTEMS AND METHODS FOR SUPPLEMENTING AN ELECTRONIC MEDICAL RECORD

(71) Applicants: Gerald T. LaBorde, Jr., Mountain Brook, AL (US); Mukul Mehra, Birmingham, AL (US)

(72) Inventors: Gerald T. LaBorde, Jr., Mountain Brook, AL (US); Mukul Mehra, Birmingham, AL (US)

(73) Assignee: Illumicare, Inc., Birmingham, AL (US)

( * ) Notice: Subject to any disclaimer, the term of this patent is extended or adjusted under 35 U.S.C. 154(b) by 1255 days.

(21) Appl. No.: 14/575,706

(22) Filed: Dec. 18, 2014

(65) Prior Publication Data

US 2017/0212989 A1    Jul. 27, 2017

(51) Int. Cl.
*G16H 10/60* (2018.01)
*G06F 3/0485* (2013.01)
*G06F 16/245* (2019.01)

(52) U.S. Cl.
CPC ........... *G16H 10/60* (2018.01); *G06F 3/0485* (2013.01); *G06F 16/245* (2019.01)

(58) Field of Classification Search
USPC ........................................................ 705/2, 3
See application file for complete search history.

(56) References Cited

U.S. PATENT DOCUMENTS

| | | | |
|---|---|---|---|
| 7,516,213 B2 | 4/2009 | Cunningham et al. | |
| 8,321,241 B1 | 11/2012 | Mansour et al. | |
| 8,412,544 B2 | 4/2013 | Reiner | |
| 8,538,776 B2 | 9/2013 | Reiner | |
| 2010/0179827 A1* | 7/2010 | McCallie, Jr. | G06Q 50/24 705/3 |
| 2012/0016685 A1 | 1/2012 | Ryan et al. | |
| 2012/0179491 A1 | 7/2012 | Liu | |
| 2013/0303870 A1 | 11/2013 | Satish et al. | |
| 2014/0046690 A1 | 2/2014 | Gunderson et al. | |

(Continued)

OTHER PUBLICATIONS

DeOrio, Lee; "Thought Leader Q&A: A 'Ribbon' Takes Top Prize;" Jan. 2018, for the Record; vol. 30 No. 1 ;pp. 26 (Year: 2018).*

(Continued)

*Primary Examiner* — Rachel L. Porter
(74) *Attorney, Agent, or Firm* — Maynard Cooper & Gale, P.C.; Jon E. Holland

(57) ABSTRACT

Systems and methods are provided to supplement an electronic record with additional information related to the electronic record. The additional information is provided to the user of the electronic record as a banner, ribbon or pop-up window that overlays or "floats" over the electronic record. The user can interact with the ribbon to obtain the additional information or ignore the ribbon and the ribbon can be hidden automatically. The ribbon can be launched in response to the user accessing a specific screen or page of the electronic record. The ribbon can provide the user with the additional information that is related to the current screen or page of the electronic record. The additional information can include information obtained from other sources that is not part of the electronic record and calculations and metrics that are not part of the electronic record.

14 Claims, 10 Drawing Sheets

(56) References Cited

U.S. PATENT DOCUMENTS

2014/0278528 A1    9/2014  Simha
2015/0205918 A1*  7/2015  Palestrant .............. G06Q 50/24
                                                               705/3

OTHER PUBLICATIONS

Microsoft UI Automation, Nov. 18, 2014, 7 pages, downloaded from http://en.wikipedia.org/wiki/Microsoft_UI_Automation.
UI Automation Overview, Nov. 18, 2014, 2 pages, downloaded from http://technet.microsoft.com/en-us/sqlserver/dd319582(v=vs.100).aspx.
UI Automation Overview, Nov. 18, 2014, 2 pages, downloaded from http://msdn.microsoft.com/en-us/library/ms747327(v=vs.110).aspx.

* cited by examiner

FIG. 3

SYSTEMS AND METHODS FOR SUPPLEMENTING AN ELECTRONIC MEDICAL RECORD

BACKGROUND

The present application generally relates to systems and methods for providing an information overlay to an electronic medical record. More specifically, the present application relates to systems and methods for providing a healthcare provider with financial and patient safety metrics to supplement the patient's clinical electronic medical record.

Each time a person, i.e., a patient, is examined or receives treatment from a healthcare provider, information regarding the patient's examination or treatment is entered and stored in a medical record for the patient. The medical record of the patient can be electronically stored by the healthcare provider as an electronic medical record (EMR) or an electronic health record (EHR). The EMR or EHR of a patient can include administrative clinical data associated with the patient such as medications, allergies, vital signs, medical history, provider/progress notes, problems, immunizations, laboratory data and/or test results and radiology reports and/or images.

When a patient is receiving treatment from a healthcare provider, the healthcare provider can make decisions regarding the patient's treatment based on the EMR of the patient. The decisions made by the healthcare provider can have a direct impact on the costs associated with the patient's treatment. However, information regarding costs is not routinely provided within the patient's EMR. In addition, the patient's EMR does not provide the healthcare provider with any information on possible health risks to the patient associated with the cumulative effect of the medications, radiographic tests, and/or laboratory tests and procedures to which the patient has been subjected.

Therefore, what is needed are systems and methods to provide a healthcare provider viewing a patient's EMR with information on utilization, expenditure and consequential risks associated with the patient's treatment by the healthcare provider.

SUMMARY

The present application generally pertains to systems and methods for supplementing an electronic record with additional information related to the electronic record. The additional information can be obtained from sources that are not directly associated with the electronic record and can supplement the information contained in the electronic record. The additional information is provided to the user of the electronic record as a banner, ribbon or pop-up window that overlays or "floats" over the electronic record. The user can interact with the ribbon to obtain the additional information or ignore the ribbon, which can result in the ribbon automatically becoming hidden after the passage of a preselected time period with no user interaction. The additional information in the ribbon can be related to the current screen, page or state of the electronic record. The present application can determine the specific screen or page of the electronic record without directly accessing the electronic record by using an accessibility framework to determine the displayed elements of the electronic record.

One advantage of the present application is that it provides a ribbon or banner of actionable intelligence that is displayed concurrently with the electronic record.

Another advantage of the present application is that the provided ribbon or banner is specific to the subject of the electronic record.

A further advantage of the present application is that the ribbon or banner can provide additional patient specific information to a patient's electronic medical record and can influence healthcare providers prospectively in the care of a patient.

Other features and advantages of the present application will be apparent from the following more detailed description of the identified embodiments, taken in conjunction with the accompanying drawings which show, by way of example, the principles of the application.

BRIEF DESCRIPTION OF THE DRAWINGS

FIG. 3 shows an embodiment of a ribbon window overlaying a page of an electronic medical record.

Wherever possible, the same reference numbers are used throughout the drawings to refer to the same or like parts.

DETAILED DESCRIPTION

Figure 1:
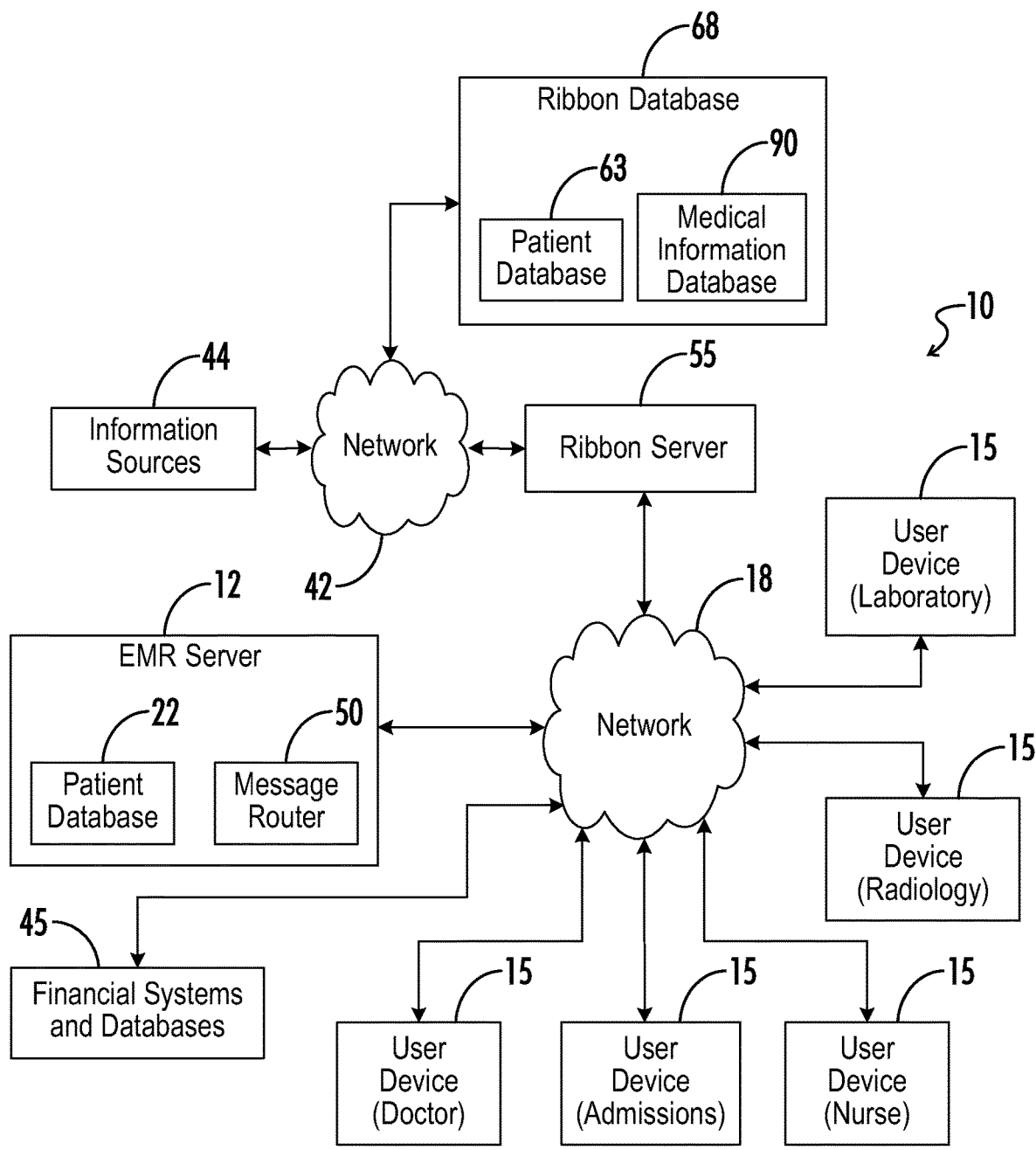
FIG. 1 is a block diagram showing an embodiment of a computer system in a medical environment.

FIG. 1 shows an embodiment of a computer system 10 for a medical or healthcare environment. The system 10 includes an EMR server 12 for hosting or executing EMR (electronic medical record) software and/or applications, which can be implemented in software, hardware, firmware or any combination thereof. The EMR application, when implemented in software, can be stored and transported on any non-transitory computer-readable medium for use by or in connection with an instruction execution apparatus, e.g., a microprocessor, that can fetch and execute instructions. The EMR software can be used to input, save and output or display information associated with a patient's EMR or EHR. The EMR server 12 can be accessed over a network 18 by one or more user devices 15 used by healthcare providers and/or departments of a medical or healthcare facility. In one embodiment, the user devices 15 can be "dummy" clients that emulate or virtualize the EMR software that is executed by the EMR server 12. However, in other embodiments, the user devices 15 can execute some or all of the EMR software and/or application independent of the EMR server 12.

The user devices 15 can be used by doctors, nurses, an admissions department, a radiology department, a laboratory and/or any other healthcare provider or department associated with the medical or healthcare facility. Each user device 15 is communicatively coupled to the network 18 to exchange (i.e., send and receive) instructions, data and/or information related to a patient's EMR with the EMR server 12. Each user device 15 can be, but is not limited to, a desktop, laptop or tablet computer, a hand-held device, such as a cellular telephone (e.g., smartphone), or attachable, wearable, implantable or non-invasive computers or devices. Each user device 15 can have one or more input devices to permit a user to enter instructions, data and/or information into the user device 15 and one or more output devices to permit the user to display instructions, data and/or information on the user device 15. In one embodiment, the network 18 can be the Internet, an Intranet, a local area network (LAN), a wide area network (WAN), or any other type of communication network using one or more communication protocols, e.g., transmission control protocol/Internet protocol (TCP/IP), to communicate over the network 18.

The EMR server 12 can store patient data for each patient in a patient database 22. The patient data for a patient can be extracted from the patient database by the EMR software and included in the patient's EMR that can be accessed by any of the user devices 15. The patient data may include one or more of the following: test results; doctor orders; documents; diagnosis; patient information; medications; allergies; patient chart; patient history; forms; immunizations; and billing information. The EMR software can display the patient's EMR on the user device 15. The patient's EMR displayed on the user device 15 may use one or more pages, screens or views to provide some or all of the patient's data to the healthcare provider.

Figure 2:
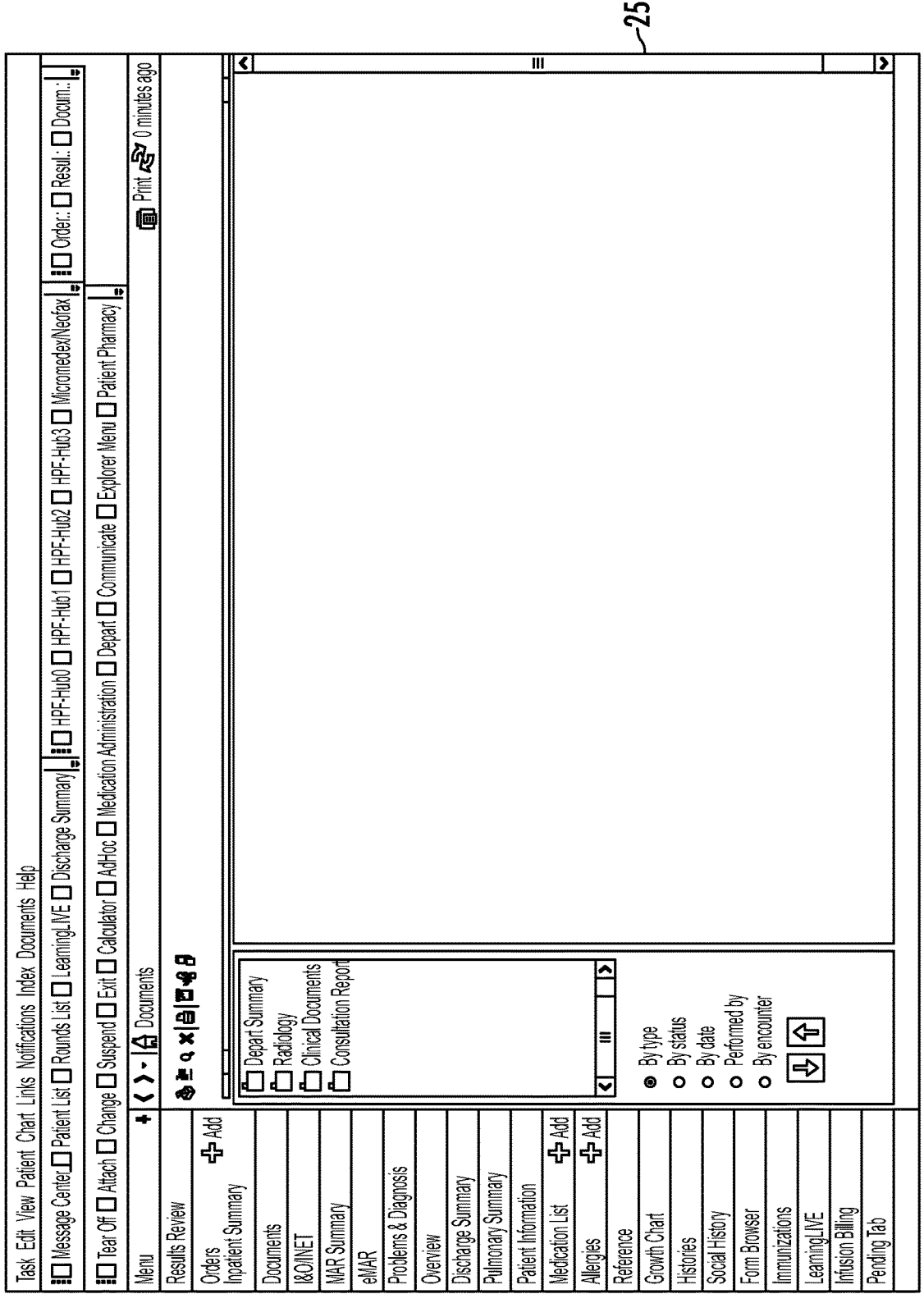
FIG. 2 shows a page of an embodiment of an electronic medical record.

FIG. 2 shows an embodiment of a page of an EMR for a patient. The EMR page 25 can include some or all of the patient's data stored in the patient database 22 and can be displayed by the user device 15. The EMR page 25 may have numerous objects or selectable icons 28 for selecting or obtaining more specific patient data from the patient database 22 stored by the EMR server 12. Depending on the object or icon 28 selected by the user, the EMR page 25 may be changed or modified to correspond to the patient data associated with the user's request.

In addition to viewing information in a patient's EMR, a healthcare provider can also input information into the displayed EMR page 25 to add to or update the patient's data stored in the patient database 22. In addition, some user devices 15 may communicate with the EMR server 12 to add information to a patient's data in the patient database 22 without using or going through the patient's EMR. When the EMR server 12 receives information from a user device 15 to update a patient's data in the patient database 22, whether the information is sent through an EMR page 25 of the patient's EMR or the information is sent through a separate message, the EMR server 12 can send a notification to other user devices 15 and/or other systems that may need to be informed of the event that generated the message to the EMR server 12. For example, information sent to the EMR server 12 from the radiology department concerning the completion of an x-ray may result in the EMR server 12 sending or forwarding a message to the medical facility's billing department to obtain payment for the completed x-ray. The EMR server 12 can include a message router 50 or interface engine to exchange, i.e., receive and distribute, messages and/or information among the user devices 15 or other systems of the medical facility.

To facilitate the transfer or sharing of information and messages among the members or components of the system 10 using computer network 18, an information sharing language or standard can be used by the message router 50, the user devices 15 and the other systems of the medical facility to define the content and structures of the information and/or messages to be communicated over the computer network 18. In one embodiment, the information sharing standard can be Health Level 7 (HL7), but the information sharing standard or language can be any suitable standard or language to facilitate communication of clinical and administrative data among components in a medical facility.

Figure 3:
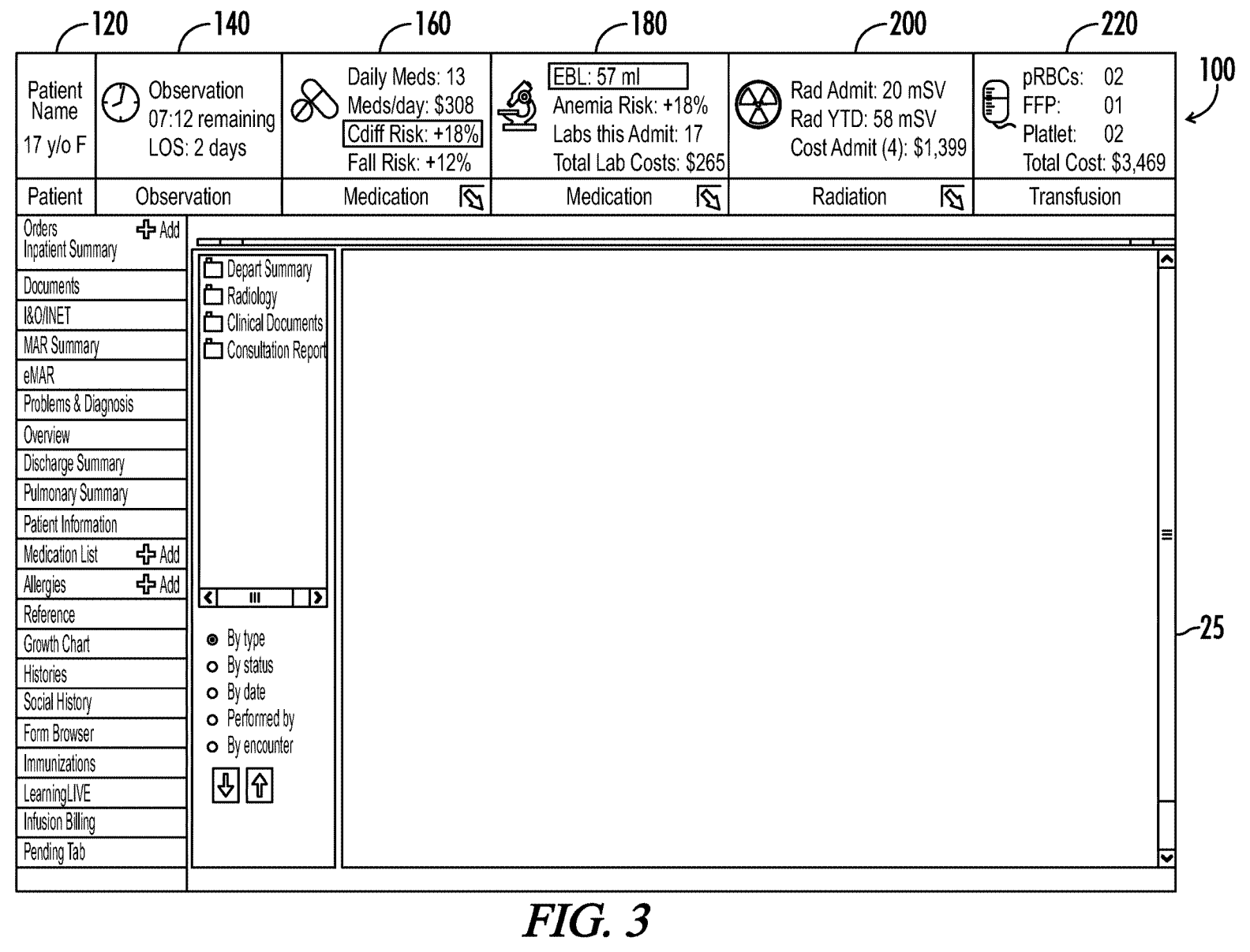

FIG. 3 shows a ribbon window providing additional patient information in conjunction with a page of a patient's EMR. A banner, ribbon or pop-up window 100 can overlay or "float" over a portion of an EMR page 25. The ribbon window 100 can be generated by executing ribbon application or software 52 (see FIG. 4). The ribbon application 52 can be installed and/or stored on each user device 15. The ribbon application 52 can be initiated or launched when the healthcare provider logs into or activates the user device 15. When a "ribbon trigger event" (e.g., navigation to an appropriate screen or page in the EMR) occurs, the ribbon application 52 can determine the current patient and launch the ribbon window 100. The ribbon application 52 on the user device 15 can communicate with the ribbon server 55 to get or obtain the appropriate patient information and data to populate or include in the ribbon window 100. The ribbon window 100 can be launched or appear over the EMR page 25 in response to specific information, data or fields being displayed in the EMR page 25, i.e., the "ribbon trigger event." To determine the specific information, data or fields being displayed in the EMR page 25, the ribbon application 52 can use or work with an accessibility framework to analyze and/or evaluate the EMR page 25 and provide the ribbon application 52 with the appropriate details and information pertaining to the EMR page 25. After receiving the information on the EMR page 25, the ribbon application 52 can evaluate the EMR page information to determine if a "ribbon trigger event" occurred and the ribbon window 100 should be launched with the EMR page 25. For example, the ribbon application 52 can launch the ribbon window 100 if the ribbon application 52 determines that specific patient information is being displayed in the EMR page 25. The ribbon application 52 can also select and configure the information to be provided in the ribbon window 100 based on the EMR page information. In alternate embodiments, the ribbon window 100 can be launched each time a user accesses an EMR page 25 or selects an object 28 on an EMR page 25 and/or the information provided or displayed in the ribbon window 100 can be predetermined regardless of the information provided in the EMR page 25.

The accessibility framework can enable applications, e.g., the ribbon application 52, to provide and consume programmatic information about user interfaces (UIs), e.g., EMR pages 25, and provide programmatic access to all or most UI elements, e.g., objects 28, on the desktop, e.g., a user device 15. The accessibility framework can expose every portion of the UI to the ribbon application 52 as an automation element. The ribbon software or application 52 can use the accessibility framework to "read" what the healthcare provider is seeing on the screen of the EMR page 25 when he/she is using the EMR software executed by the EMR server 12. Everything on the screen of the EMR page 25 can be a readable "automation element" using the accessibility framework. The automation element can provide or expose common properties of the UI element the automation element represents. One type of property can be the textual content. The textual content can be a text stream that represents the contents of a text container along with format and style attributes. Another type of property can be the control type which defines basic appearance and functionality. The automation elements can also provide or expose control patterns that provide properties, e.g., an expand and collapse ability or a selection mechanism, specific to one or more control types. The accessibility framework can also provide information to the ribbon software 52 through events. The ribbon software 52 can receive event notifications from the accessibility network concerning specific events that occur in the EMR page 25. The event notifications can provide information on the automation element that triggered the event and other properties and control pattern information associated with the event. In one embodiment, the accessibility framework can be Microsoft UI Automation, but could be other types of accessibility frameworks in other embodiments.

The ribbon application 52 inspects the automation elements to determine, among other things, the healthcare provider or doctor viewing the EMR, the patient associated with the EMR, and the current screen of the EMR page 25 being viewed by the healthcare provider. In one embodiment, the ribbon application 52 can determine the healthcare provider or doctor viewing the EMR, the patient associated with the EMR, and the current screen of the EMR page 25 by reading the textual content properties of the automation elements. In another embodiment, the ribbon application 52 can determine the current screen of the EMR page 25 by analyzing the control type and other properties of the automation elements to determine the configuration and arrangement of the elements displayed on the screen. By reviewing the automation elements from the accessibility framework, the ribbon application 52 can launch the ribbon window 100 on the appropriate EMR pages 25, for the right patient and track how that particular healthcare provider uses the ribbon window 100.

Once launched, the ribbon window 100 can remain displayed over the EMR page 25 for a preselected time period. If the user does not interact with the ribbon window 100, such as by scrolling over a portion of the ribbon window 100, within the preselected time period, the ribbon window 100 can automatically close or be hidden leaving the entire EMR page 25 displayed for the user. In one embodiment, the preselected time period can be in the range of 3 seconds to 20 seconds. If the ribbon window 100 is closed or hidden, the ribbon window 100 can be reopened by selecting an icon or link that is made available or presented to the user. However, if the user does interact with the ribbon window 100, the ribbon window 100 can remain open until closed by the user. In another embodiment, once the user interacts with the ribbon window 100, the ribbon window 100 can stay open until a preselected time period of user inactivity with the ribbon window 100 has elapsed. The preselected time period of user inactivity can be the same time period as the preselected time period for interaction or a different time period.

The ribbon window 100 can display additional information related to a patient's EMR in one or more frames, sections or fields. In one embodiment shown in FIG. 3, the ribbon window 100 can include a patient frame 120, an observation frame 140, a medication frame 160, a laboratory frame 180, a radiation frame 200 and a transfusions frame 220. The patient frame 120 can provide the user with the name, age and sex of the patient. The healthcare provider or user can then use the information in the patient frame 120 to verify that the patient and patient information in the ribbon window 100 corresponds to the patient and patient information in the EMR page 25. The observation frame 140 can provide the user with information on the time remaining in an observation period for the patient and information on the patient's length of stay (LOS) in the medical facility. The medication frame 160 can provide the user with information on the number of daily medications for the patient, the cost of the daily medications for the patient, the patient's relative risk of a *Clostridium difficile* (*C. diff*) infection, the patient's risk of falling and the enzymatic pathways related to medication metabolism. The laboratory frame 180 can provide the user with information on the estimated blood loss (EBL) of the patient from laboratory procedures, the patient's medical facility or hospital acquired anemia (HAA) risk, the number of laboratory procedures for the patient and the cost of the laboratory procedures for the patient. The radiation frame 200 can provide the user with an estimate of the amount of radiation the patient has received since being admitted to the medical facility, an estimate on the amount of radiation the patient has received this year and the associated cost of the radiation procedures since the patient was admitted to the medical facility. The transfusions frame 220 can provide the user with information on how many units of packed red blood cells (pRBCs) the patient has received, how many units of fresh frozen plasma (FFP) the patient has received, how many units of platelets the patient has received and the associated cost of the transfusions. In one embodiment, the frames presented to the user and/or the contents of the frames within the ribbon window 100 can be dependent on user interaction with the ribbon window 100. In another embodiment, the frames or sections included in the ribbon window 100 can be dependent on the patient information being displayed in the EMR page 25 and/or on the availability of additional patient data for a particular frame or section.

When the ribbon window 100 is launched, the ribbon application 52 can populate the sections or frames of the ribbon window 100 with clinical data and metrics, financial data and/or other appropriate additional patient information obtained from the ribbon sever 55. The ribbon server 55 can be connected over a network 42 to outside information sources 44, e.g., published research studies, Medicare and Medicaid databases, wholesale acquisition cost (WAC) and average wholesale price (AWP) databases and medical reference databases and manuals, to obtain or generate some of the information included in the ribbon window 100. In one embodiment, the network 42 can be the Internet, an Intranet, a local area network (LAN), a wide area network (WAN), or any other type of communication network using one or more communication protocols, e.g., transmission control protocol/Internet protocol (TCP/IP), to communicate over the network 42. Further, while network 18 and network 42 are shown as separate networks in FIG. 1, network 18 and network 42 can be combined or can be the same network in another embodiment.

The ribbon server 55 can also be connected to information sources that are internal to or within the medical or healthcare facility to obtain or generate some of the information included in the ribbon window 100. For example, the ribbon server 55 can access a healthcare facility's financial systems or databases 45, e.g., a drug acquisition cost database, a pharmacy database, a radiology database, a supply chain database and/or a cost accounting system, over network 18 to obtain or generate some of the information included in the ribbon window 100. In one embodiment, the healthcare facility's financial systems or databases 45 can be stored or included in EMR server 12.

Figure 4:
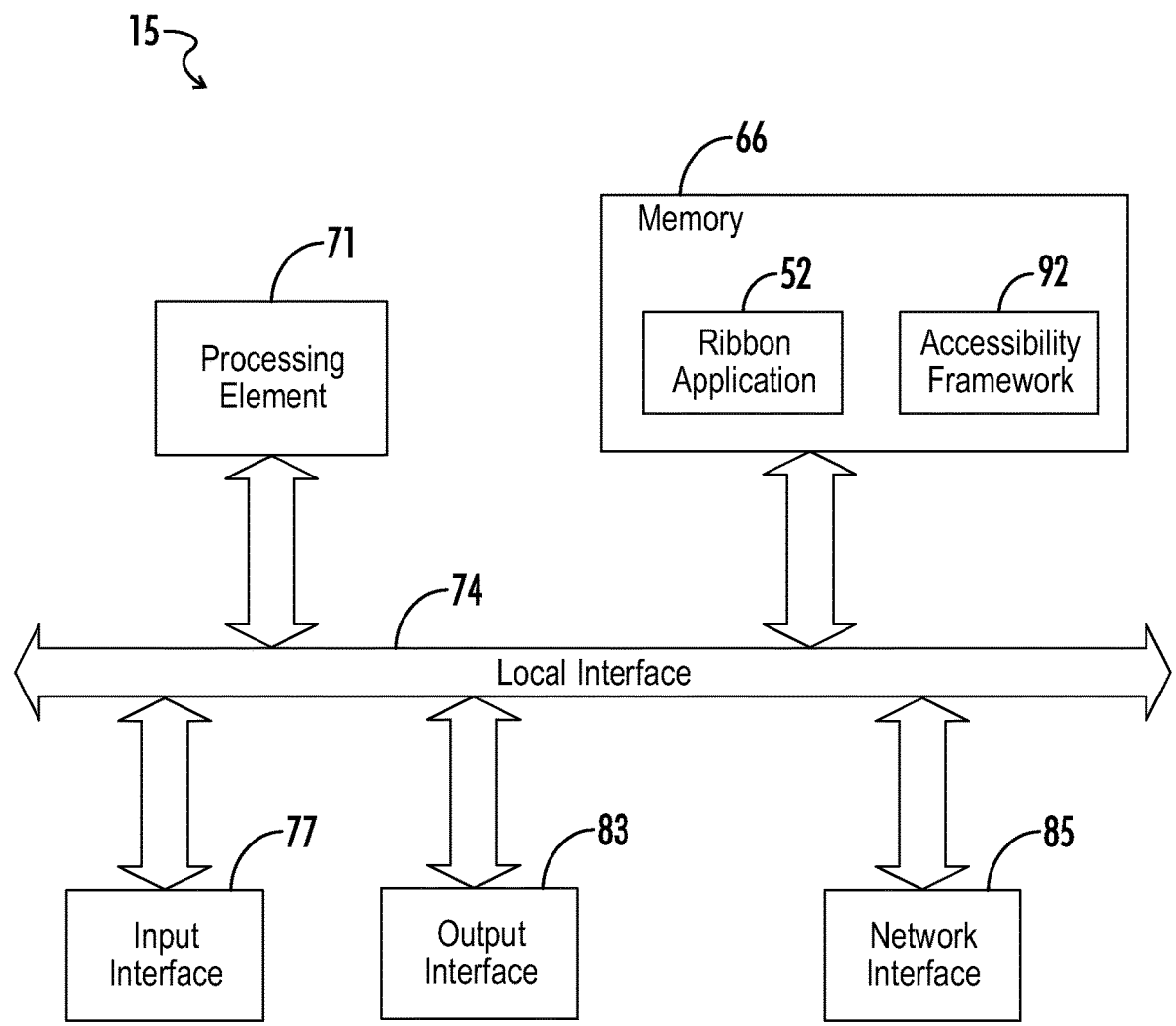
FIG. 4 is a block diagram showing an embodiment of a user device.

FIG. 4 shows an embodiment of the user device 15. The user device 15 includes the ribbon application 52, which can be implemented in software, hardware, firmware or any combination thereof. In the user device 15 shown in FIG. 4, the ribbon application 52 can be implemented in software and stored in memory 66. The ribbon application 52, when implemented in software, can be stored and transported on any non-transitory computer-readable medium for use by or in connection with an instruction execution apparatus, e.g., a microprocessor, that can fetch and execute instructions. In the context of this application, a "computer-readable medium" can be any device, system or technique that can contain or store a computer program for use by or in connection with an instruction execution apparatus.

The user device 15 shown by FIG. 4 includes at least one conventional processing element 71, such as a digital signal processor (DSP) or a central processing unit (CPU), that communicates to and drives the other elements within the user device 15 via a local interface 74, which can include at least one bus. Furthermore, an input interface 77, for example, a keyboard or a mouse, can be used to input data from a user of the user device 15, and an output interface 83, for example, a printer, monitor, liquid crystal display (LCD), or other display apparatus, can be used to output data to the user of the user device 15. A network interface 85, such as at least one modem, may be used to exchange data with the network 18.

The ribbon application 52 can use information stored in a central ribbon database 68 when preparing and assembling the information for the ribbon window 100. The ribbon application 52 can request the information for the ribbon window 100 from the ribbon server 55 which can then access the ribbon database 68 (see FIG. 1) over the network 42 to obtain the appropriate information for the ribbon window 100. In another embodiment, the ribbon database 68 can be stored in memory of the ribbon server 55.

The ribbon database 68 can be implemented in software, hardware, firmware or any combination thereof on either the ribbon server 55 or on a separate computer or hardware device as shown in FIG. 1. In one embodiment, the ribbon database 68 can be implemented in software and stored in a memory device. The ribbon database 68, when implemented in software, can be stored and transported on any non-transitory computer-readable medium for use by or in connection with an instruction execution apparatus, e.g., a microprocessor, that can fetch and execute instructions. In the context of this application, a "computer-readable medium" can be any device, system or technique that can contain or store a computer program for use by or in connection with an instruction execution apparatus.

The ribbon server 55 and the ribbon database computer can each include at least one conventional processing element, such as a digital signal processor (DSP) or a central processing unit (CPU), that communicates to and drives the other elements within the ribbon server 55 or the ribbon database computer via a local interface, which can include at least one bus. Furthermore, an input interface, for example, a keyboard or a mouse, can be used to input data from a user of the ribbon server 55 or the ribbon database computer and an output interface, for example, a printer, monitor, liquid crystal display (LCD), or other display apparatus, can be used to output data to the user of the ribbon server 55 or the ribbon database computer. A network interface(s), such as at least one modem, may be used by the ribbon server 55 or the ribbon database computer to exchange data with the network 18 and/or network 42.

The ribbon database 68 can include patient data and information stored in a patient database 63 (see FIG. 1) and information stored in a medical information database 90 (see FIG. 1). The information in medical information database 90 can include information relating to published research studies, Medicare and Medicaid databases, wholesale acquisition cost (WAC) databases and medical reference databases and manuals that was obtained from information sources 44 (see FIG. 1) not associated with computer network 18. The information in medical information database 90 can also include information obtained from the healthcare facility's financial systems or databases 45. The patient database 63 can include, for each patient, patient data that was obtained from the network 18 and/or EMR server 12 and/or patient data that was obtained from other sources not connected to network 18. In one embodiment, the patient data from other sources can be obtained over network 42. The ribbon database 68 can also include computations, categorizations, and/or derivations of data from either or both of the patient database 63 and the medical information database 90.

Information for the patient database 63 can be obtained from messages received over the network 18 by the ribbon server 55. The ribbon server 55 can be copied or included in communications or messages between the user devices 15 and the EMR server 12 over the network 18. A message listener in the ribbon server 55 can be used to monitor the communications over the network 18 to obtain information for the patient database 63. When a message or communication is received by the message listener and the ribbon server 55, the message can be parsed by the ribbon server 55 into one or more individual segments. The segments can then be reviewed to determine if the segments have information related or relevant to information to be provided in the ribbon window 100. The relevant information from the segments of the parsed message can be saved in the patient database 63 (based the patient who was the subject of the message) and the information and/or segments that are not used or required for the ribbon window 100 can be discarded or ignored. Since the patient database 63 does not store all of the information obtained from a parsed message, the patient data in patient database 63 can be different from the patient data in patient database 22. In addition, the patient database 63 can include additional patient data from other sources that are separate from or not connected to the network 18.

As previously discussed, the ribbon application 52 can receive information from the accessibility framework 92 to determine when to launch the ribbon window 100 with the EMR page 25. The accessibility framework 92 can include an application programming interface (API) that can communicate directly with the API on the user device 15.

The ribbon window 100 can provide the healthcare provider with a broader patient "context" than can be found in the patient's EMR by enabling the healthcare provider to access additional information that is related to or relevant to the patient. For example, the observation frame 120 can provide the healthcare provider with information on how long the patient has been under observation or, alternatively, how much time is remaining in insurance defined observation periods. Information on the amount of time the patient has been under observation is important to the healthcare provider because if the patient is under observation for greater than a specified observation period, e.g., 48 hours, the patient's health insurance may not reimburse the healthcare provider and/or the medical facility for any costs incurred after the expiration of the observation period. The non-reimbursed costs may then have to be absorbed by the healthcare provider and/or medical facility.

Other frames of the ribbon window 100 can provide additional information and/or detail when the healthcare provider selects or interacts with the frames. The ribbon window 100 can transform into an expanded frame window to provide additional information for a particular frame. In one embodiment, the medication frame 160, the laboratory frame 180 and the radiation frame 200 can all provide additional information and details when selected by the healthcare provider.

Figure 5:
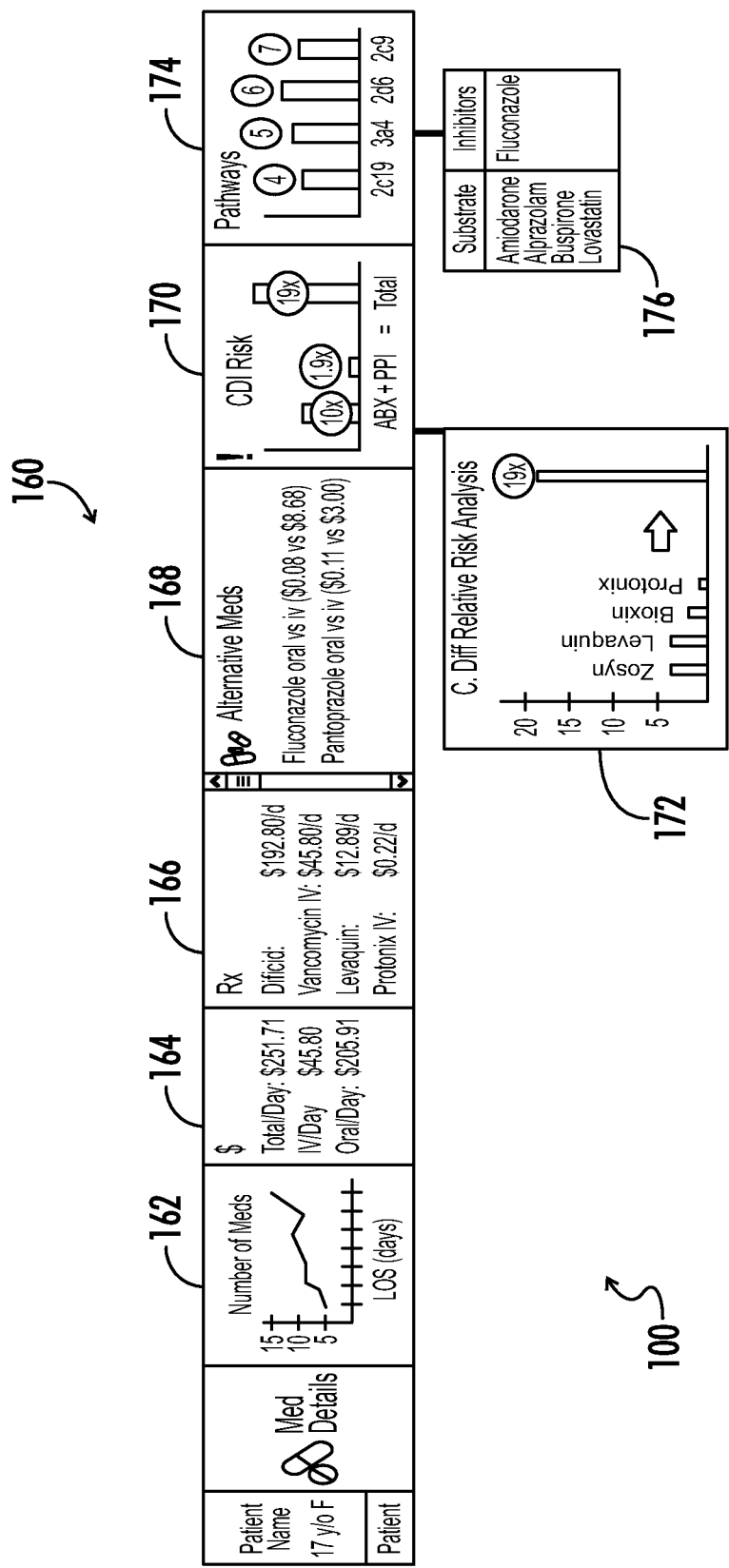
FIG. 5 shows an embodiment of the ribbon window displaying additional information for a medication frame.

FIG. 5 shows an embodiment of the ribbon window displaying additional information for a medication frame. The medication frame 160 can include one or more additional frames or sections to provide additional or supplemental information on the medications being provided to the patient. The displaying of the additional frames and/or additional information in the medication frame 160 can be dependent on the information available in the ribbon database 68. In other words, the ribbon application 52 may not display particular information or a particular frame in the medication frame 160 if there is no corresponding information from the ribbon database 68.

A number of medications frame 162 can provide the healthcare provider with a graph showing the number of medications administered to the patient over the patient's length of stay (LOS) at the medical facility. A medication cost frame 164 can provide the healthcare provider with a total cost of medications administered to the patient and the cost of the medications administered orally and intravenously. The ribbon database 68 can calculate the medication costs by reviewing the list of medications for the patient from the patient database 63, correlating the corresponding cost information from the medical information database 90 to the identified medications and adding the individual costs. In one embodiment, the medication cost information in the medical information database 90 can be obtained from a wholesale acquisition cost database (information source 44) over the network 42. In another embodiment, the medication cost information in the medical information database 90 can include cost information obtained from the healthcare facility's financial systems or databases 45 such as a pharmacy database and/or a supply chain database. A prescription cost frame 166 can provide the healthcare provider with the cost of the individual prescriptions for the patient. The cost of the individual prescriptions is determined similar to the cost of the medications. An alternative medication frame 168 can provide the healthcare provider with recommendations on alternative medications that have a lower cost and show the healthcare provider the difference in cost. The ribbon database 68 can review the patient's medications and information from medical information database 90 to determine if there is a similar lower cost medication available to treat the patient's condition instead of the current medication and then provide the lower cost medication information to the ribbon application 52 for display in the ribbon window 100. For example, an oral medication may be a lower cost substitute for the intravenous form of the medication if the patient can accept an oral medication.

A CDI relative risk frame 170 can provide the healthcare provider with information on the patient's real-time risk for potentially acquiring a *Clostridium difficile* infection (CDI) based on the medications received by the patient. The CDI risk frame 170 can also provide a CDI risk incorporating the antibiotics (ABXs) taken by the patient and the proton pump inhibitors (PPIs) or acid blockers taken by the patient. If the healthcare provider requires more information, a medication-specific CDI risk frame 172 can be accessed from the CDI risk frame 170 by interacting with the CDI risk frame 170. A medication-specific CDI risk frame 172 can be used to provide the CDI risk for each of the medications taken by the patient.

Figure 6:
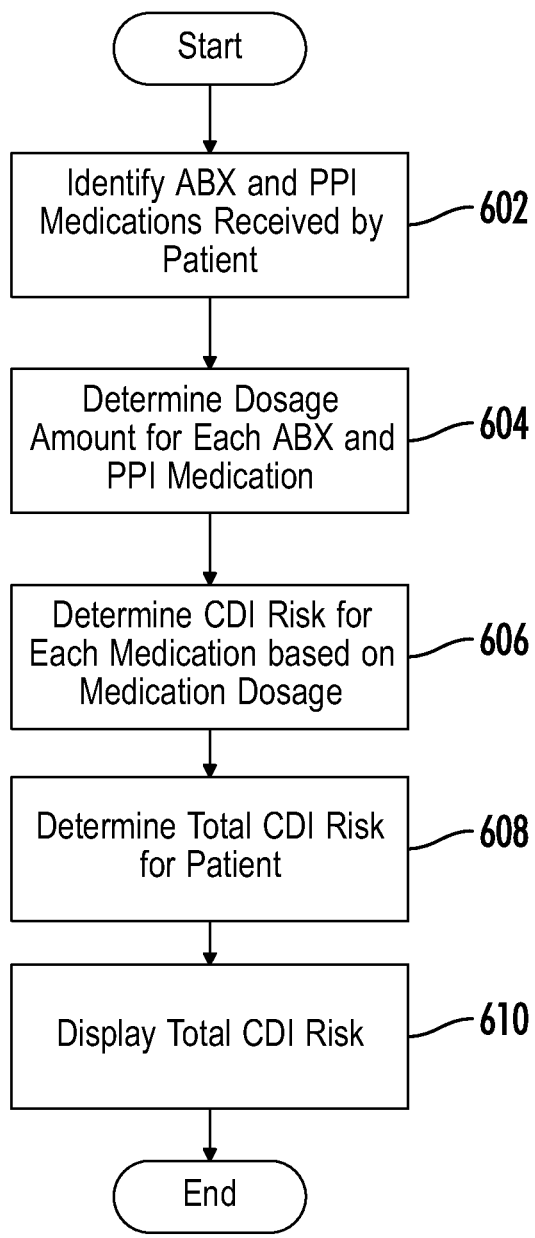
FIG. 6 shows an embodiment of a process for calculating a patient's risk of a *Clostridium difficile* infection.

FIG. 6 shows an embodiment of a process for calculating a patient's relative risk of a CDI. The process begins with the ribbon database 68 identifying the patient's medications that are classified as an ABX or as a PPI (step 602). Some examples of ABXs can include piperacillin, levofloxacin and clarithromycin. Some examples of PPIs can include pantoprazole and esomeprazole. To identify the patient's ABX and PPI medications, the ribbon database 68 accesses and reviews the patient data from the patient database 63 and medication information from the medical information database 90 to determine which medications are classified as an ABX or a PPI. The patient database 63 can include information on the patient's medications obtained from messages from the EMR server 12.

Once the ribbon database 68 has identified the ABX and PPI medications, the ribbon database 68 then determines the ordered dosage of each of the scheduled medications (step 604). The ribbon database 68 can obtain the dosage of the medication directly from the patient data if the patient was provided a dose of only that medication. However, if the dosage of a medication to a patient includes multiple medications, such as from a combination medication formed from multiple medications, the ribbon database 68 can analyze the dosage of the combination medication to determine the dosage of the individual medications. The ribbon database 68 can determine the dosage of each of the individual medications in the combination medication, or the ribbon database 68 can determine the dosage of only the ABX or PPI medications in the combination medications. The ribbon database 68 can first determine the dosage of the medications as a weight or volume, e.g., mg or ml, and then convert the weight or volume dosage to a unit dosage that reflects the dosage amount relative to a manufacturer recommended dose (defined daily dose (DDD)). For example, a half dose of a medication may be 0.5 units, a recommended dose of the medication may be 1.0 units and a double dose of the medication may be 2.0 units. In one embodiment, the ribbon database 68 can adjust the risk of CDI from a medication based on the defined daily dose of the medication administered to the patient. The ribbon database 68 can then use information from the medical information database 90 to determine the adjusted current *Clostridium difficile* relative risk at a given point in time.

Once the ribbon database 68 has calculated the dosage of each ABX or PPI medication, the ribbon database 68 then calculates or determines the CDI risk to the patient for each of the ABX or PPI medications (step 606). The ribbon database 68 can calculate the patient's adjusted CDI relative risk for each ABX or PPI medication by taking the medication type and the dosage of the medication and generating a risk value for the patient using formulas and/or medical research (possibly stored in and obtained from medical information database 90) that correlate CDI risk to the dosage amount for that medication. The relative risk of CDI can be the multiple of the individual dose-adjusted risks for each antibiotic the patient is currently receiving and a multiple of the risk associated with a proton pump inhibitor, if the patient is currently receiving that class of medication. The adjusted CDI relative risk adjusts in real-time as the medication profile changes. A CDI risk profile can be provided for a given medication profile rather than for a patient profile as the patient profile does not attempt to adjust for demographic or prior factors that affect CDI. The medication profile can be a more important metric in its value in promoting judicious antibiotic and PPI stewardship. In one embodiment, the ribbon database 68 can calculate the adjusted CDI risk for each medication under the assumption that a recommended dose (or ordered dose) of medication was provided for the patient. After calculating the initial CDI risk for each medication, the ribbon database 68 can adjust, i.e., increase or decrease, the patient's CDI risk based on whether the patient actually received less than or greater than the recommended dose. For example, a patient receiving double the recommended dose of a medication may result in a doubling of the patient's adjusted CDI risk for that medication.

The ribbon database 68 can then take the individual CDI risks from each of the medications and determine the patient's total CDI risk (step 608). The patient's total CDI risk can be obtained by multiplying the composite adjusted PPI CDI risk and the composite adjusted ABX CDI risk. The composite ABX CDI risk can be determined by multiplying the individual adjusted ABX CDI risks. The ribbon database 68 can then provide the patient's total CDI risk to the ribbon application 52 for display in the ribbon window 100 (step 610).

A pathways frame 174 can provide the healthcare provider with information on the number of medications being metabolized in particular enzymatic or metabolic pathways. If the healthcare provider requires more information, an individual pathway frame 176 can be accessed from the pathways frame 174 by interacting with the pathways frame 174. The individual pathway frame 176 can be used to provide a list of the medications using the particular pathway and some or all of the medication's properties (inducer, substrate or inhibitor) with respect to that pathway.

Figure 7:
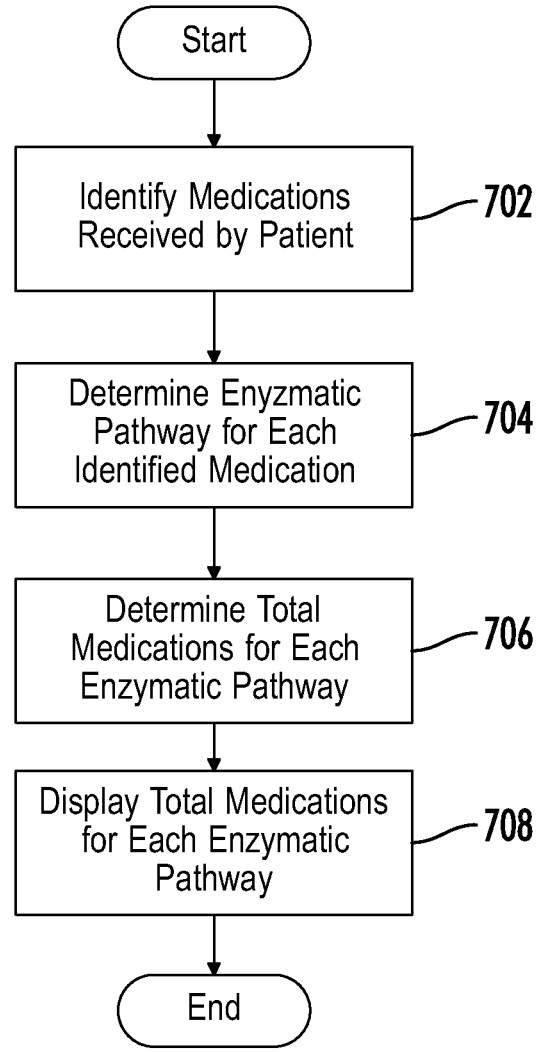
FIG. 7 shows an embodiment of a process for calculating the number of medications using an enzymatic pathway.

FIG. 7 shows an embodiment of a process for calculating the number of medications using an enzymatic pathway. The process begins with the ribbon database 68 identifying the patient's medications (step 702). To identify the patient's medications, the ribbon database 68 accesses and reviews the patient data from the patient database 63. The patient database 63 can include information on the patient's medications obtained from messages from the EMR server 12. Next, the ribbon database 68 determines the enzymatic pathway for each of the medications (step 704) by reference to the medical information database 90. Some examples of enzymatic pathways can include the cytochrome P450 (CYP) superfamily of enzymes and more specifically the CYP1A2, CYP2C9, CYP2C19, CYP2D6, CYP3A4, and CYP3A5 enzymes. Once the enzymatic pathway for the medications is determined, if applicable, the ribbon database 68 then determines the medication's properties with relation to the enzymatic pathway, i.e., is the medication is an inhibitor, which decreases or blocks metabolic activity, an inducer, which increases metabolic activity, or a substrate, which has consumptive activity on the available enzyme. The ribbon database 68 can use information from the medical information database 90 to determine the medication's enzymatic pathway and properties with respect to the enzymatic pathway. After determining the enzymatic pathway for each of the applicable medications, the ribbon database 68 can then add the number of medications using each enzymatic path to get a total number of medications using each enzymatic pathway (step 706). The ribbon database 68 can then provide the number of medications using each enzymatic pathway to the ribbon application 52 for display in the ribbon window 100 (step 708). The ribbon application 52 can also display the medications using an enzymatic pathway (as determined and provided to the ribbon application 52 by the ribbon database 68) and the medications' properties with respect to that pathway (as determined and provided to the ribbon application 52 by the ribbon database 68) in individual pathway frame 176.

The pathway information can be useful to the healthcare provider to predict or prevent adverse drug reactions in the medical facility setting. An enzymatic pathway has a limited capacity to metabolize medications and if that capacity is altered by an inhibitor or an inducer medication or overloaded by too many medications using the enzymatic pathway, the patient may have an adverse drug reaction and/or the effectiveness of an administered medication may decline and impact the treatment of the patient as manifested by potential side effects of the medications. The healthcare provider can use the information regarding the pathway usage from the pathways frame 174 and individual pathway frame 176 to determine if a particular medication may be impacting the effectiveness of the patient's treatment or may be in conflict with another medication. In one embodiment, the ribbon database 68 can also use information on the patient's pharmacogenomic profile (PGx) from the patient database 63, e.g., the patient is a slow metabolizer along particular genetic pathways, to generate information displayed by ribbon application 52 to assist the healthcare provider in determining whether the patient is on the proper medication regimen.

Figure 8:
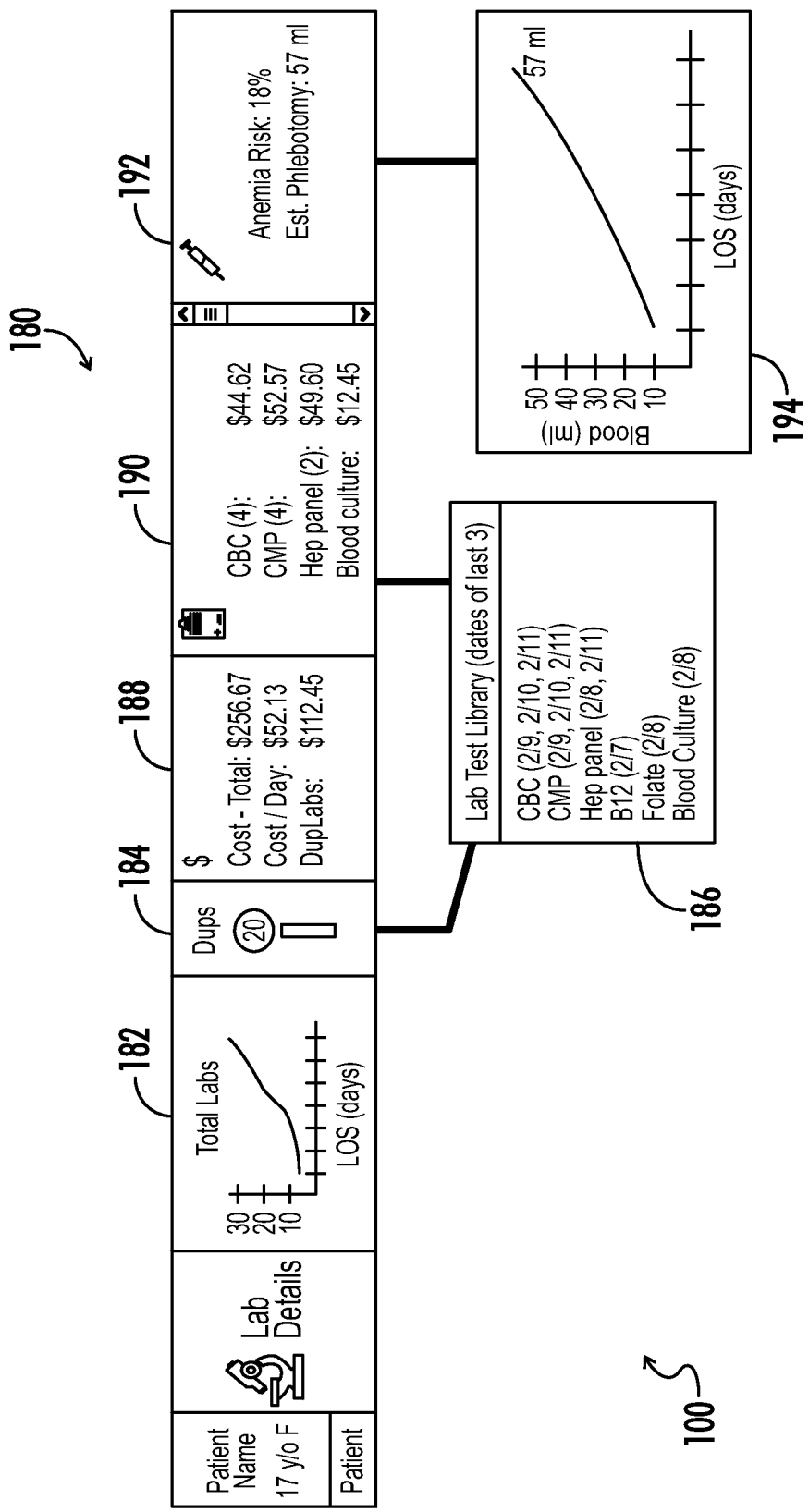
FIG. 8 shows an embodiment of the ribbon window displaying additional information for a laboratory frame.

FIG. 8 shows an embodiment of the ribbon window displaying additional information for a laboratory frame. The laboratory frame 180 can include one or more additional frames or sections to provide additional or supplemental information on the laboratory procedures or tests being performed on the patient. The displaying of the additional frames and/or additional information in the laboratory frame 180 can be dependent on the information available in the ribbon database 68. In other words, the ribbon application 52 may not display particular information or a particular frame in the laboratory frame 180 if there is no corresponding information from the ribbon database 68.

A number of laboratories frame 182 can provide the healthcare provider with a graph showing the number of laboratory procedures performed on the patient during the patient's LOS at the medical facility. A number of duplicate procedures frame 184 can provide the healthcare provider with information on the number of times the same laboratory procedure(s) have been performed on a patient. If the healthcare provider requires more information, a lab test library frame 186 can be accessed from the duplicate procedures frame 184 by interacting with the duplicate procedures frame 184. The lab test library frame 186 can provide a list of all laboratory procedures performed on the patient and the dates the laboratory procedures were performed. In one embodiment as shown in FIG. 8, the dates of the most recent three laboratory procedures can be provided.

A laboratory cost frame 188 can provide the healthcare provider with a total cost of laboratory procedures performed on the patient, the cost of laboratory procedures performed on the patient for the current day and the cost associated with the performance of duplicate laboratory procedures on the patient. The ribbon database 68 can calculate the laboratory costs by reviewing the list of laboratory procedures for the patient from the patient database 63, correlating the corresponding cost information from the medical information database 90 to the identified laboratory procedures and adding the individual costs. In one embodiment, the laboratory cost information in medical information database 90 can be obtained from a Medicare allowable charges database (information source 44) over the network 42. In another embodiment, the laboratory cost information in the medical information database 90 can include cost information obtained from the healthcare facility's financial systems or databases 45. A laboratory procedure cost frame 190 can provide the healthcare provider with the total cost of the individual laboratory procedures performed on the patient. The total cost of the individual laboratory procedures is determined similar to the cost of all of the laboratory procedures. If the healthcare provider requires more information, the lab test library frame 186 can also be accessed from the laboratory procedure cost frame 190 by interacting with the laboratory procedure cost frame 190. As previously described, the lab test library frame 186 can provide a list of all available laboratory procedures performed on the patient and the dates the laboratory procedures were performed.

An anemia risk frame 192 can provide the healthcare provider with information on the patient's risk of medical facility acquired anemia due to laboratory procedures or blood draws and an estimated blood loss (EBL) from phlebotomy procedures. The patient's risk of medical facility acquired anemia is calculated by the ribbon database 68 using the estimate of the amount of blood drawn from the patient. If the healthcare provider requires more information, an amount of blood drawn frame 194 can be accessed from the anemia risk frame 192 by interacting with the anemia risk frame 192. The amount of blood drawn frame 194 can provide a graph of the total EBL or estimated blood drawn from the patient during the patient's LOS at the medical facility.

Figure 9:
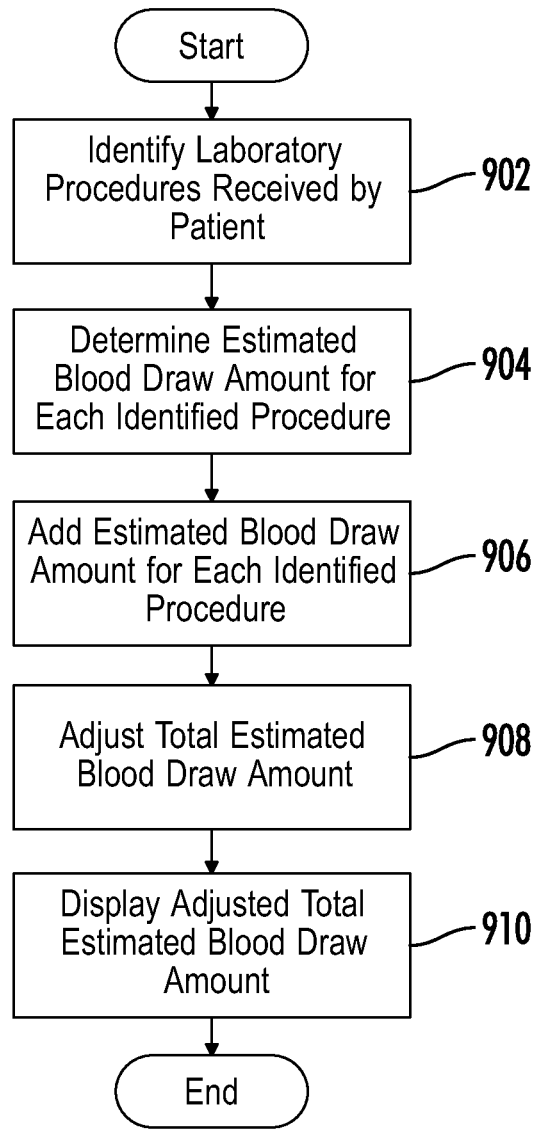
FIG. 9 shows an embodiment of a process for calculating an amount of blood drawn from a patient.

FIG. 9 shows an embodiment of a process for calculating an EBL or amount or volume of blood drawn from a patient. The process begins with the ribbon database 68 identifying the laboratory procedures performed on the patient (step 902). Some examples of laboratory procedures can include a CBC (complete blood count) test, a CMP (comprehensive metabolic panel) test, a Hep (hepatitis) panel, a cardiac or heart enzyme study, a B12 test, a folate or folic acid test, and a blood culture test. To identify the patient's ordered and executed laboratory procedures, the ribbon database 68 accesses and reviews the patient data from the patient database 63. The patient database 63 can include laboratory procedure information obtained from messages from the EMR server 12.

Once the ribbon database 68 has the identified laboratory procedures, the ribbon database 68 then determines an estimated blood draw amount for each identified procedure (step 904). The ribbon database 68 can obtain an estimated blood draw amount for each procedure from the medical information database 90. The estimated blood draw amount or volume for each procedure stored in the medical information database 90 can be based on medical research and can be determined as an average blood draw amount or volume for the laboratory procedure order or request. In one embodiment, the ribbon database 68 can calculate the average blood draw amount for a laboratory procedure based on information regarding the particular sample tube used for the procedure, if available, and/or information on the medical facility performing the procedure, if available. The ribbon database 68 can then add the estimated blood draw amount for each identified laboratory procedure to obtain a total estimated blood draw amount or volume (step 906).

However, a medical facility may perform multiple laboratory procedures on one blood sample drawn from the patient. To account for this possibility and provide a more accurate estimate of the blood draw amount for the patient, the ribbon database 68 can adjust the total estimated blood draw amount or volume (step 908). When determining whether to adjust the total estimated amount of blood draw, the ribbon database 68 first looks at the laboratory procedures performed on the patient and identifies procedures that cannot be adjusted because the laboratory test requires a fresh blood sample, e.g., a CBC test or a heart enzyme test, rather than being acquired from a previous blood draw. Once the ribbon database 68 identifies the procedures that cannot be adjusted (or assumed to be a zero volume laboratory), the ribbon database 68 reviews the executed laboratory procedures to determine if some laboratory procedures could have used a single blood sample. If more than one of the laboratory procedures has results provided within a predetermined time period, e.g., 24 hours, and the laboratory procedure is assigned a tube type (i.e., color) that has already been drawn and utilized by the phlebotomy department, the ribbon database 68 can assume that those multiple procedures were performed from a single blood sample. The ribbon database 68 can group the procedures and lower the total estimated blood draw amount by the corresponding estimated blood draw amount for all of the procedures except for the procedure with the largest estimated blood draw amount. In one embodiment, the ribbon database 68 can estimate the total blood draw amount, for a cluster of laboratory procedures, as being the volume of one tube, if the non-excluded procedures over a 24 hour period can be drawn from the same tube. The ribbon database 68 can then provide the adjusted estimated total blood draw amount to the ribbon application 52 for display in the ribbon window 100 (step 910).

The adjusted estimated total blood draw amount from a patient can then be stored in the patient database 63 for use by the ribbon database 68 to determine the patient's real time medical facility acquired anemia risk as provided in frame 192. The ribbon database 68 can calculate the patient's medical facility acquired anemia risk by taking the adjusted estimated total blood draw amount of the patient from the patient database 63 and using the adjusted estimated total blood draw amount to generate a risk value for the patient using formulas and/or medical research (possibly stored in medical information database 90) that correlate medical facility acquired anemia risk to the adjusted estimated total blood draw amount. In one embodiment, for every 50 mL of blood drawn, the patient's risk of medical facility acquired anemia can be an incremental 15%. In another embodiment, the ribbon database 68 can use the stored adjusted estimated total blood draw amount to calculate a new adjusted estimated total blood draw amount if the patient receives additional laboratory procedures.

Figure 10:
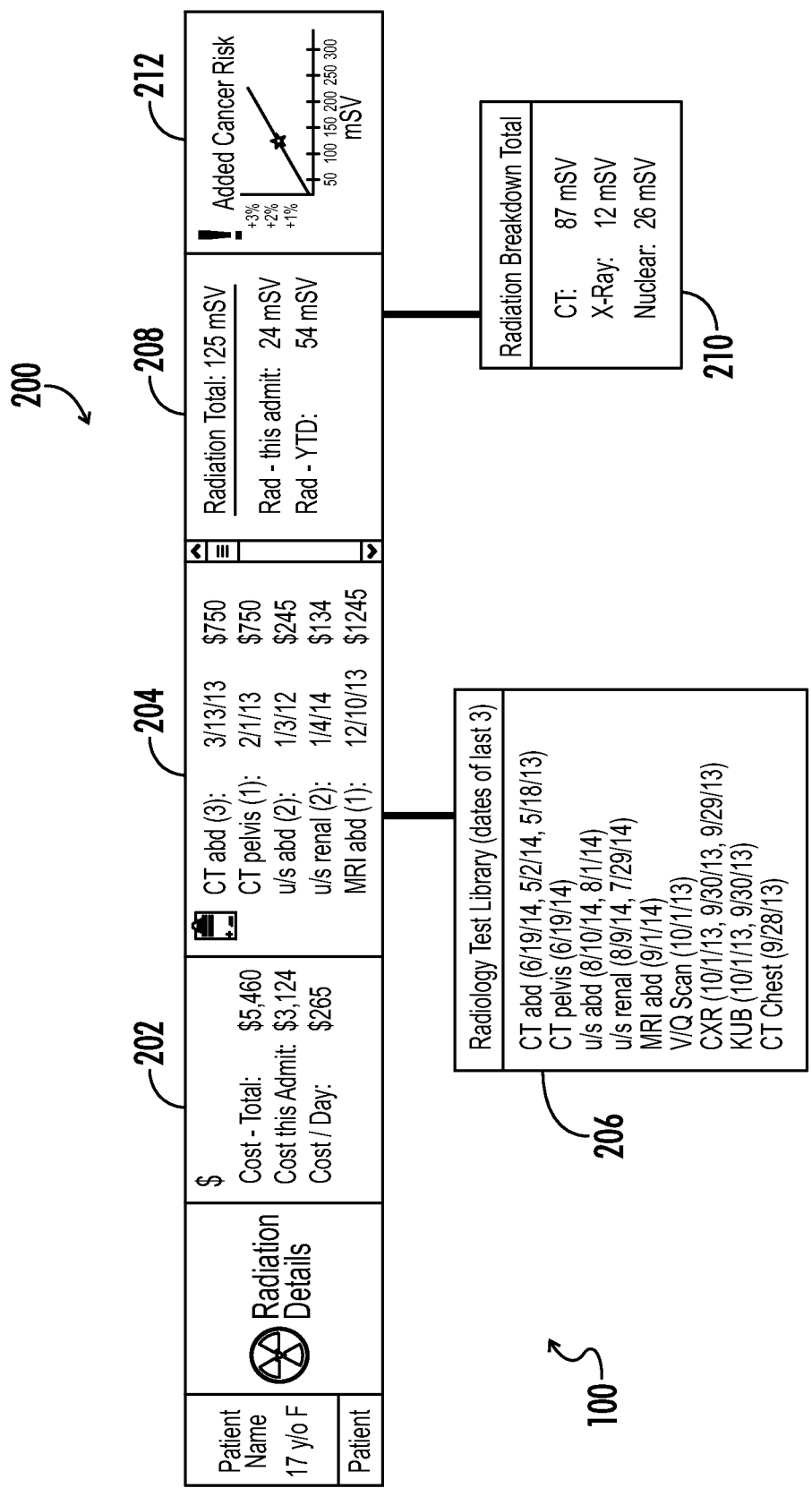
FIG. 10 shows an embodiment of the ribbon window displaying additional information for a radiation frame.

FIG. 10 shows an embodiment of the ribbon window displaying additional information for a radiation frame. The radiation frame 200 can include one or more additional frames or sections to provide additional or supplemental information on radiation treatments or procedures being provided to the patient. The displaying of the additional frames and/or additional information in the radiation frame 200 can be dependent on the information available in the ribbon database 68. In other words, the ribbon application 52 may not display particular information or a particular frame in the radiation frame 200 if there is no corresponding information from the ribbon database 68.

A radiology cost frame 202 can provide the healthcare provider with a total cost of radiology procedures performed on the patient, the cost of radiology procedures performed on the patient while the patient has been admitted to the medical facility and the cost of radiology procedures performed on the patient for the current day. The ribbon database 68 calculates the radiology procedure costs by reviewing the list of radiology procedures for the patient in the patient database 63, correlating the corresponding cost information from the medical information database 90 to the identified radiology procedures and then adding the individual costs. In one embodiment, the radiology cost information in medical information database 90 can be obtained from a Medicare allowable charges database (information source 44) over the network 42. In another embodiment, the radiology cost information in the medical information database 90 can include information obtained from the healthcare facility's financial systems or databases 45 such as a radiology database or system.

A radiology procedure cost frame 204 can provide the healthcare provider with the total cost of the individual radiology procedures performed on the patient. The total cost of the individual radiology procedures is determined similar to the cost of all of the radiology procedures. If the healthcare provider requires more information, the radiology test library frame 206 can be accessed from the radiology procedure cost frame 204. The radiology test library frame 206 can provide a list of all radiology procedures performed on the patient and the dates the radiology procedures were performed. In one embodiment as shown in FIG. 10, the dates of the most recent three radiology procedures can be provided.

An estimated radiation frame 208 can provide the healthcare provider with an estimated effective dose of radiation in milliSieverts (mSV), due to medical imaging, received by the patient for his/her life, an estimate of the effective dose of radiation received by the patient while the patient has been admitted to the medical facility and an estimate of the effective dose of radiation received by the patient for the calendar year, i.e., a year-to-date (YTD) total. If the healthcare provider requires more information, the radiation breakdown frame 210 can be accessed from the estimated radiation frame 208 by interacting with the estimated radiation frame 208. The radiation breakdown frame 210 can provide a list of all radiology procedures performed on the patient and an estimate of the total effective dose of radiation received for the radiology procedures. A cancer risk frame 212 can provide the healthcare provider with a graph and information on the patient's absolute risk of cancer based on the total effective dose of radiation received by the patient over his/her life.

Figure 11:
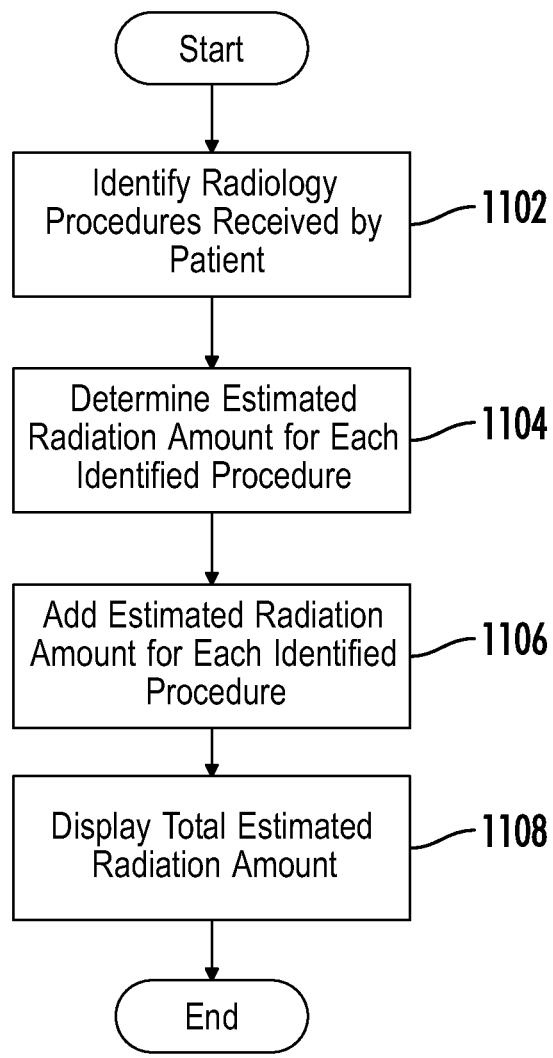
FIG. 11 shows an embodiment of a process for calculating a patient's estimated radiation.

FIG. 11 shows an embodiment of a process for calculating a patient's estimated effective dose of radiation from medical imaging and other procedures. The process begins with the ribbon database 68 identifying the radiology procedures received by the patient (step 1102). Some examples of radiology procedures can include x-rays, CT (computed tomography) scans and nuclear medicine scans. To identify the patient's ordered and executed radiology procedures, the ribbon database 68 accesses and reviews the patient data from the patient database 63. The patient database 63 can include radiology procedure information obtained from messages from the EMR server 12 and/or obtained from other medical facilities, systems and/or databases. If an estimated total effective dose of radiation is being provided for a time period less than the patient's life, e.g., a daily total or a LOS total, then the ribbon database 68 filters out the radiology procedures not in the desired time period. Once the ribbon database 68 has the identified radiology procedures, the ribbon database 68 then determines an estimated effective dose of radiation for each identified procedure (step 1104). The ribbon database 68 can obtain an estimated effective dose of radiation for each procedure from the medical information database 90. The estimated effective dose of radiation for each procedure can be based on medical research and can be determined as an average effective dose of radiation for the procedure based on multiple imaging estimates being taken from multiple facilities and multiple devices. The ribbon database 68 can then add the estimated effective dose of radiation for each identified radiology procedure to obtain a total estimated effective dose of radiation (step 1106). The ribbon database 68 can then provide the total estimated effective dose of radiation to the ribbon application 52 for display in the ribbon window 100 (step 1108).

The estimated total effective dose of radiation received by a patient can then be stored in the patient database 63 for use by the ribbon database 68 to determine the patient's real time cancer risk as provided in frame 212. The ribbon database 68 can calculate the patient's cancer risk by taking the total estimated effective dose of radiation received by the patient from the patient database 63 and using the total estimated effective dose of radiation to generate a risk value for the patient using formulas and/or medical research (possibly stored in medical information database 90) that correlate cancer risk to the total estimated effective dose of radiation. In one embodiment, the patient's risk of cancer can linearly increase by 1% for every 100 mSV of radiation (effective dose). In another embodiment, the ribbon database 68 can use the stored estimated total effective dose of radiation to calculate a new estimated total effective dose of radiation if the patient has received additional radiology procedures.

In one embodiment of the present application, the ribbon database 68 can pre-calculate, i.e., calculate before being requested by the ribbon application 52, one or more of the patient's risks or metrics, e.g., enzymatic pathway information, EBL or effective dose of radiation, based on information stored in the patient database 63 and the medical information database 90. The pre-calculated risks or metrics for the patient can be stored in either the ribbon database 68 or the patient database 63 for immediate access and use by the ribbon application 52. In other embodiments, the ribbon database 68 can dynamically calculate the patient's risks and metrics when the information is required or requested by the ribbon application 52 for the ribbon window 100.

Embodiments within the scope of the present application include program products with machine-readable media for carrying or having machine-executable instructions or data structures stored thereon. Machine-readable media can be any available non-transitory media that can be accessed by a general purpose or special purpose computer or other machine with a processor. By way of example, machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communication connection (either hardwired, wireless, or a combination of hardwired or wireless) to a machine, the machine properly views the connection as a machine-readable medium. Combinations of the above are also included within the scope of machine-readable media. Machine-executable instructions include, for example, instructions and data which cause a general purpose computer, special purpose computer, or special purpose processing machine to perform a certain function or group of functions.

Although the figures herein may show a specific order of method steps, the order of the steps may differ from what is depicted. Also, two or more steps may be performed concurrently or with partial concurrence. Variations in step performance can depend on the software and hardware systems chosen and on designer choice. All such variations are within the scope of the application. Software implementations could be accomplished with standard programming techniques, with rule based logic and other logic to accomplish the various connection steps, processing steps, comparison steps and decision steps.

It should be understood that the identified embodiments are offered by way of example only. Other substitutions, modifications, changes and omissions may be made in the design, operating conditions and arrangement of the embodiments without departing from the scope of the present application. Accordingly, the present application is not limited to a particular embodiment, but extends to various modifications that nevertheless fall within the scope of the application. It should also be understood that the phraseology and terminology employed herein is for the purpose of description only and should not be regarded as limiting.

What is claimed is:

1. A computer implemented method of providing additional information to an electronic medical record of a patient, the method comprising:

initiating a ribbon application on a user device;

accessing, with the ribbon application, a plurality of elements associated with a plurality of displayed objects from a page of an electronic medical record displayed by an EMR application on the user device, wherein the plurality of elements are generated from an additional application separate from the EMR application, and the ribbon application accesses the plurality of elements without accessing the EMR application;

each element of the plurality of elements including information about one or more properties of a corresponding displayed object of the plurality of displayed objects from the displayed page of the electronic medical record, and wherein the page of the electronic medical record includes first information associated with a patient stored in a first server computer;

identifying, with the ribbon application, the page of the electronic medical record displayed by the EMR application and the patient associated with the first information included in the page of the electronic medical record based on the information about the properties of the displayed objects from the plurality of elements accessed by the ribbon application;

detecting an occurrence of a trigger event associated with the page of the electronic medical record;

launching, with the ribbon application, a window on the user device to display second information associated with the identified patient in response to the trigger event; overlaying a portion of the page of the electronic medical record displayed by EMR application with the launched window;

obtaining, by the ribbon application, the second information based on the identified page of the electronic medical record and the identified patient from a second server computer, the second information being different from the first information, wherein said obtaining the second information comprises calculating, by the second server computer, at least one metric using the second information associated with the identified patient and additional medical information stored in the second server computer;

wherein said calculating at least one metric includes at least one of calculating an estimated blood loss for the identified patient, calculating an effective dose of radiation received by the identified patient, calculating a risk for a *Clostridium difficile* infection, calculating a risk of anemia from blood loss or calculating a risk of cancer from received radiation; and populating the launched window with the obtained second information associated with the identified patient.

2. The method of claim 1, wherein the additional application comprises an accessibility framework and said accessing the plurality of elements includes providing the plurality of elements to the ribbon application with the accessibility framework executed by a processor of the user device.

3. The method of claim 1, wherein said identifying the page of the electronic medical record and the patient associated with the first information included in the page of the electronic medical record includes reviewing text information in the plurality of elements, wherein the text information is obtained from the one or more properties of the plurality of displayed objects.

4. The method of claim 1, further comprising closing the launched window in response to a predetermined time period elapsing without a user interaction with the launched window.

5. The method of claim 1, further comprises storing the calculated at least on metric as second information associated with the identified patient in the second server computer.

6. The method of claim 1, wherein said launching a window on the user device comprises providing a plurality of frames in the launched window, the plurality of frames includes two or more frames selected from the group consisting of a patient frame with information on the identified patient, an observation frame with information on a length of stay at a medical facility by the identified patient, a medication frame with information on medications received by the identified patient, a laboratory frame with information on laboratory procedures performed on the identified patient, a radiation frame with information on radiation received by the identified patient or a transfusions frame with information on transfusions received by the identified patient.

7. The method of claim 6, further comprising transforming, by the ribbon application, the launched window in response to a user selection of the medication frame, the laboratory frame or the radiation frame, the transformed window includes an additional portion of the second information associated with the identified patient from the second server computer, the additional portion of the second information is selected by the ribbon application in response to the identified patient and the selected frame.

8. The method of claim 1, further comprising generating, by the second server computer, at least a portion of the second information from one or more messages received from the first server computer and associated with the identified patient.

9. The method of claim 8, wherein said generating at least a portion of the second information comprises:

parsing the one or more messages received from the first server computer into a plurality of segments;

reviewing each segment of the plurality of segments for information relevant to the identified patient; and storing the relevant information in the second server computer as second information for the identified patient.

10. The method of claim 1, wherein said detecting the occurrence of the trigger event includes analyzing the plurality of elements to identify the trigger event.

11. The method of claim 1, wherein the trigger event includes one or more of a predetermined page of the electronic medical record being displayed or a predetermined field being included in the displayed page of the electronic medical record.

12. The method of claim 1, wherein the one or more properties include a textual content property and a control type property, wherein the textual content property represents a text stream of a text container in the corresponding displayed object of the electronic medical record and the control type property defines an appearance and functionality of the corresponding displayed object of the electronic medical record.

13. The method of claim 1, further comprising:
   maintaining the launched window in an open state in response to a user interaction with the launched window; and
   closing the launched window in response to an action by the user.

14. The method of claim 1, wherein the ribbon application is installed on the user device and executed by a processor of the user device.

* * * * *